(12) United States Patent
Guldager et al.

(10) Patent No.: US 10,493,230 B2
(45) Date of Patent: Dec. 3, 2019

(54) INTERMITTENT URINARY CATHETER

(71) Applicant: Coloplast A/S, Humlebaek (DK)

(72) Inventors: Pernille Merethe Guldager, Lyngby (DK); Klaus Weye Fredskilde, Helsingoer (DK); Marie Terese Nalbandian, Holte (DK)

(73) Assignee: Coloplast A/S, Humlebaek (DK)

( * ) Notice: Subject to any disclaimer, the term of this patent is extended or adjusted under 35 U.S.C. 154(b) by 226 days.

(21) Appl. No.: 15/104,981

(22) PCT Filed: Dec. 19, 2014

(86) PCT No.: PCT/DK2014/050445
§ 371 (c)(1),
(2) Date: Jun. 16, 2016

(87) PCT Pub. No.: WO2015/090338
PCT Pub. Date: Jun. 25, 2015

(65) Prior Publication Data
US 2017/0028168 A1 Feb. 2, 2017

(30) Foreign Application Priority Data
Dec. 20, 2013 (DK) .................................. 2013 70808

(51) Int. Cl.
*A61M 25/00* (2006.01)
(52) U.S. Cl.
CPC ...... *A61M 25/0017* (2013.01); *A61M 25/007* (2013.01); *A61M 25/0021* (2013.01); *A61M 2025/0046* (2013.01); *A61M 2025/0059* (2013.01); *A61M 2025/0073* (2013.01); *A61M 2210/1092* (2013.01)

(58) Field of Classification Search
CPC .......... A61M 25/0023; A61M 25/0017; A61M 25/0021; A61M 25/007; A61M 2025/0073
See application file for complete search history.

(56) References Cited

U.S. PATENT DOCUMENTS

| | | | |
|---|---|---|---|
| 3,831,814 A * | 8/1974 | Butler | A61M 5/162 222/81 |
| 4,406,656 A * | 9/1983 | Hattler | A61M 25/0009 604/103.14 |
| 4,894,057 A | 1/1990 | Howes | |
| 5,295,962 A * | 3/1994 | Crocker | A61F 2/88 604/101.02 |
| 6,190,349 B1 * | 2/2001 | Ash | A61M 25/0021 138/115 |
| 2004/0172009 A1 * | 9/2004 | Marisi | A61F 5/4405 604/544 |

(Continued)

FOREIGN PATENT DOCUMENTS

CN 202277602 U 6/2012
DE 102006052612 B3 2/2008
(Continued)

*Primary Examiner* — Kai H Weng
(74) *Attorney, Agent, or Firm* — Coloplast Corp., Coloplast A/S; Nick Baumann

(57) ABSTRACT

An intermittent urinary catheter 1 with a generally triangular cross-section with three substantially flat surfaces 7a, 7b, 7c connected by rounded corners 8a, 8b, 8c and at least one eyelet 6, 10 positioned in one of the surfaces is described.

16 Claims, 3 Drawing Sheets

(56) References Cited

U.S. PATENT DOCUMENTS

| | | | |
|---|---|---|---|
| 2006/0135980 A1* | 6/2006 | Trinidad | A61M 25/1002 606/191 |
| 2011/0319902 A1 | 12/2011 | Epstein | |
| 2012/0239005 A1* | 9/2012 | Conway | A61M 25/0017 604/544 |
| 2013/0253479 A1 | 9/2013 | Su | |

FOREIGN PATENT DOCUMENTS

| GB | 2418361 A1 | 3/2006 |
|---|---|---|
| RU | 2008031 C1 | 2/1994 |
| WO | 2009010975 A1 | 1/2009 |

\* cited by examiner

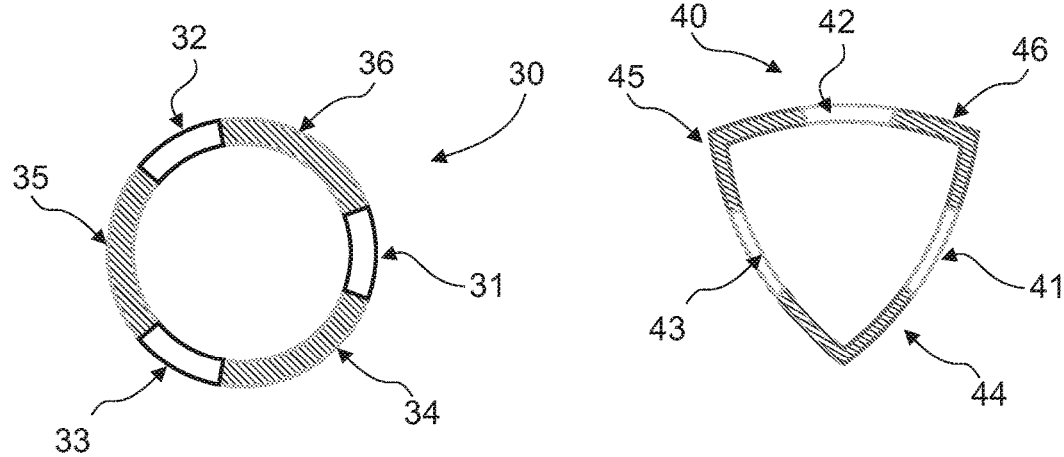
Fig. 8
Fig. 9
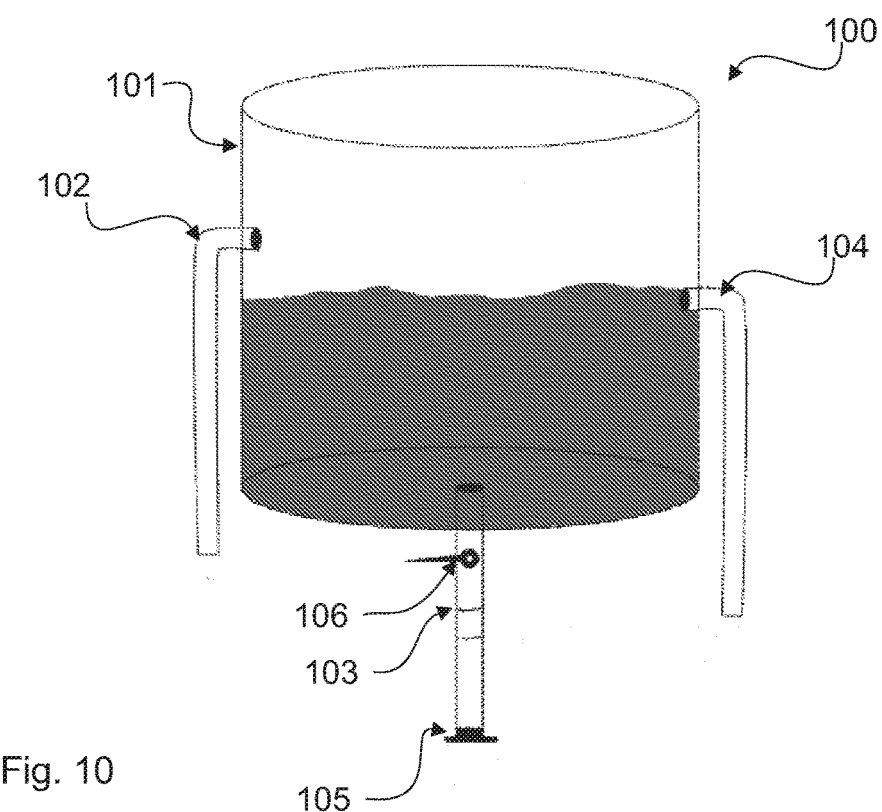
Fig. 10

INTERMITTENT URINARY CATHETER

BACKGROUND

Urinary catheter assemblies for draining the bladder are increasingly used for intermittent catheterisation. Typically, urinary catheters are used by patients suffering from urinary incontinence or by disabled individuals like paraplegics or tetraplegics, who may have no control permitting voluntary urination and for whom catheterisation may be the way of urinating.

Intermittent catheters are typically inserted by the user him- or herself and sits only in the urethra and bladder for as long as it takes to empty the bladder—e.g. for about 5-10 minutes. Intermittent catheters are used every 4-6 hours to empty the bladder corresponding roughly to the interval at which people having no urinary problems would usually go to the bathroom. An important feature for the intermittent catheter is to ease the insertion into the urethra. This is done by providing the intermittent catheter with a low frictious surface. Non-limiting examples of such are hydrophilic coated catheters which are subsequently wetted by a swelling media in order to produce a low friction surface, or oil or water based gel which is applied to the catheter before insertion into the urethra.

Intermittent urinary catheters may be provided with a hydrophilic coating that needs to be wetted prior to use and thereby absorbs a considerable amount of liquid. Such a hydrophilic coating will provide a very lubricious surface that has very low-friction when the catheter is to be inserted.

Users of intermittent catheters may experience that emptying of the bladder takes long time—e.g. more than 10-15 minutes. This may at least partly be due to the fact that the user is unable to provide any pressure to the bladder, e.g. if the user is somehow spinal cord injured. This means that the urine has to exit the bladder through the catheter only through gravity forces. Furthermore, the limitation in the diameter of the catheter may also influence the flow-rate. The volumetric flow rate for a female that is not a catheter user is in average 25 ml/s—however flow rates down to 15 ml/s are within the normal margin.

SUMMARY OF THE INVENTION

The invention relates to an intermittent urinary catheter as defined in claim 1.

BRIEF DESCRIPTION OF THE DRAWING

FIGS. 8 and 9 illustrate cross sections of catheters having three eyelets at the same height. FIG. 8 illustrates a catheter with a circular cross section and FIG. 9 illustrates a catheter with a triangular cross section.

FIG. 10 illustrates a test set-up used for the experiments.

DETAILED DESCRIPTION OF THE INVENTION

Figure 1:
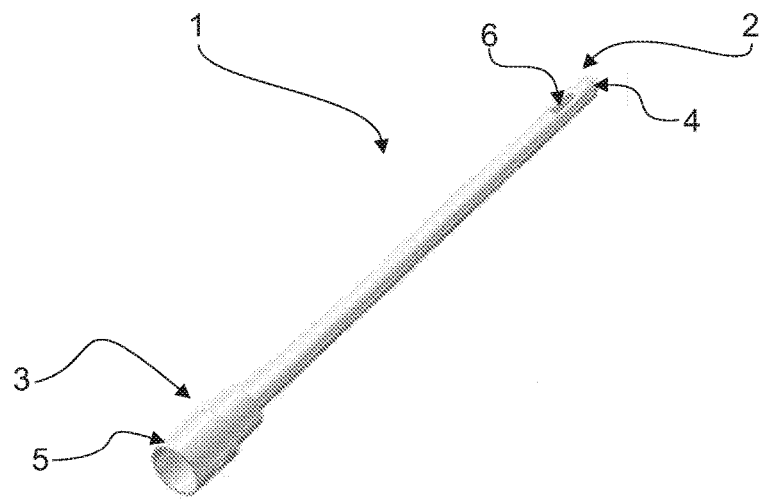
FIG. 1 illustrates a perspective view of an embodiment of a catheter according to the invention.

In embodiments, the intermittent urinary catheter is generally triangular in cross-section—this allows positioning of the eyelets in substantially flat surfaces and thus reduction of chafing at the mucosal surfaces of the urethra. Another aspect of the invention relates to positioning at least two eyelets in the same height at the urinary catheter—that is equidistantly from the tip. More eyelets positioned at the same height will allow for an increase in flow because more liquid can enter into the catheter and be drained out from the bladder. An interesting embodiment relates to a conical catheter. Conical catheters will lead to a more laminar flow, which provides a better flow than a more turbulent flow.

In a first aspect, the invention relates to an intermittent urinary catheter with a generally triangular cross-section with three substantially flat surfaces connected by rounded corners and at least one eyelet positioned in one of the surfaces.

A catheter with a triangular cross-section has a higher buckling strength than a catheter with a round cross-section. This means that the wall thickness of the catheter can be reduced in a triangular catheter and thus a larger inner cross-sectional area can be achieved.

Furthermore, the eyelets can be positioned in substantially flat surfaces on the sides of the catheter. When eyelets are positioned in a substantially flat surface the entire edge of the eyelet will be in the same plane—that is the plane that corresponds to the surface. When eyelets are positioned in a round surface, the edge of the eyelets will be curved in three dimensions. This means that parts of the edge, more specifically, the parts in the longitudinal direction of the catheter, will be positioned in another (lower) plane than the parts in the transverse direction of the catheter. The mucosa of the urethra may have a tendency to collapse around the catheter during insertion, thus if the edge of an eyelet is three-dimensional and thus has parts positioned lower than other parts, the mucosa may be slightly caught at the lower parts during insertion. This may lead to a degree of chafing at the mucosa during insertion. A plane or two-dimensional eyelet positioned in a substantially flat surface will minimise this effect, because there will be no lower positioned parts of the eyelet—thus the chafing caused by this will be eliminated.

By substantially flat surfaces is meant that seen in cross section, the length of the curve defining the surface between two corners are only slightly longer (less than 15%, or more preferred less than 10%, such as less than 5%) than the chord between the same two corners. In other words, the surface area of one side of the catheter is less than 15% (such as less than 10% or less than 5%) larger than the area of the plane spanned by the two corners of the side.

By rounded corners is meant that the transition from one surface to another around a circumferential cross-section of the catheter follows a rounded curve.

Another way of describing this is that the cross-section of the catheter consists of three pieces having a first small curvature (large radius) joined alternately with three pieces having a second larger curvature (small radius). The small radius (the corners) may be between 1 mm and 1.7 mm such as 1.4 mm or 1.5 mm, whereas the large radius may be more than 10 mm.

In an embodiment of the invention, the three substantially flat surfaces are of generally the same size. By generally the same size is meant that the surfaces have generally the same area meaning that the variation in area between the surfaces is lower than 5%.

In the following, whenever referring to a proximal end of an element of the invention, the referral is to the end adapted for insertion. Whenever referring to the distal end of an element, the referral is to the end opposite the insertion end. In other words, the proximal end is the end closest to the user, when the catheter is to be inserted and the distal end is the opposite end—the end furthest away from the user when the catheter is to be inserted.

The longitudinal direction is the direction from the distal to the proximal end. The transverse direction is the direction perpendicular to the longitudinal direction, which corresponds to the direction across the shaft of the catheter.

The catheters described in this application are adapted for use as a urinary catheter.

The catheter comprises a main tubular part extending from the distal end to the proximal end. The tip is positioned in the proximal end of the catheter and is provided as a rounded closed end of the tube constituting the main part of the catheter. Eyelet(s) for letting urine enter into the catheter is typically positioned close to the tip. The catheter may comprise a connector in the distal end and may in an embodiment comprise a flared end of the catheter so that the diameter of the connector increases with respect to the tubular part. The catheter may also comprise a handle in the distal end, which has a length allowing the user to manipulate the catheter.

Usually catheters used as urinary draining devices and adapted for intermittently being inserted into the urethra to drain urine from the bladder, are from size 8 FR to size 18 FR. FR (or French size or Charriere (Ch)) is a standard gauge for catheters approximately corresponding to the outer circumference in mm. More accurately, the outer diameter of the catheter in mm corresponds to FR divided by 3. Thus 8 FR corresponds to a catheter with an outer diameter of 2.7 mm and 18 FR corresponds to a catheter with an outer diameter of 6 mm.

A catheter used as urinary draining devices (a urinary catheter) which is adapted for intermittently being inserted into the urethra to drain urine from the bladder is adapted for being inserted by the user him/herself without assistance from medical personal and without insertion of any type of aids (e.g. guidewires) prior to insertion of the urinary catheter.

The eyelets may have an area at the surface of the catheter of between 3-5 mm².

For the triangular catheters of this invention, the correlation between the CH sizes and the triangular catheters is so that the cross-sectional area inside the catheter corresponds to the cross-sectional area inside the corresponding CH size. Thus the CH size corresponds neither to the inscribed circle of the triangle nor to the circumscribed circle of the triangle. Rather comparing the triangular cross-section with the corresponding CH size, the CH size is between the inscribed circle and the circumscribed circle of the triangle.

The circumference of a triangular catheter is defined (the usual way) as the sum of the side lengths in the cross-section.

Catheters of this invention may prior to use be provided with a hydrophilic coating so as to impart a low-friction insertion.

The hydrophilic coating may be provided only on the insertable part of the catheter. The hydrophilic surface coating is of the kind which, when hydrated or swelled using a swelling medium, reduces the friction on the surface area of the catheter which is intended to be inserted into the urinary channel of a user corresponding to the insertable part of the catheter.

An intermittent hydrophilic catheter differs from an indwelling catheter in that the hydrophilic surface coating of such a catheter is not suitable for indwelling use, because the surface coating tends to stick inside the mucosa of the urethra if left inside the body for a period exceeding 5-20 minutes, due to the hydrophilic coating transforming from being highly lubricious when fully wetted (95% weight water) to being adhesive when the hydration level of the coating is reduced (<75% weight water).

In a second aspect, the invention relates to an intermittent, urinary catheter, where the catheter is provided with two eyelets positioned equidistantly from the tip of the catheter.

Eyelets positioned equidistantly from the tip are an advantage, because the urine will flow where the resistance is lowest meaning that urine would rather flow in the bladder than flow inside the catheter due to the lower resistance in the bladder than in the catheter. This means that if the eyelets were positioned with a different distance to the tip, then the eyelet closer to the tip would contribute less than the eyelet furthest from the tip—provided that the lowermost eyelet is inserted fully into the bladder so urine can flow freely into this eyelet. In other words, the urine will mostly run through the eyelets closest to the outlet to avoid the higher resistance inside the catheter for as long as possible.

Thus, positioning of two eyelets with the same distance to the tip ensures that both eyelets will contribute to lead the urine into the catheter.

In an embodiment, the catheter is provided with three eyelets positioned equidistantly from the tip of the catheter.

Three eyelets will provide for an even better emptying of the bladder.

Increasing the total area of the eyelets (the sum of the areas of each eyelet) will lead to an increased inflow of urine into the catheter. However, the catheter is only able to drain as much urine as the cross-sectional area of the catheter allows. This is because the volumetric flow rate follows the following principle:

The resistance equals the pressure difference divided by the volumetric flow rate.

The above can be expressed in the form of an equation:

$$R = \frac{\Delta P}{Q} = \frac{(8\mu L)}{\pi a^4} \tag{1}$$

In the equation above, R is the resistance to flow, ΔP is the pressure difference, Q is the volumetric flow rate, μ is the fluid viscosity, L is the length and a is the cross-sectional area.

Thus the volumetric flow rate Q can be expressed as:

$$Q = \frac{\Delta P \cdot \pi a^4}{8\mu L} \tag{2}$$

From the equation above, it is clear that the cross-sectional area has a great influence on the volumetric flow rate. Thus, the cross-sectional area is the main factor on how fast the urine can be drained through the catheter.

This means that if the total area of the eyelets can be as large as (or even exceed) the cross-sectional area of the catheter at the eyelets, then the cross-sectional area is utilised to the optimum degree.

Due to the above consideration relating to urine flowing where the resistance is as small as possible, it is most beneficiary to increase the width of the eyelets (transversely of the catheter) rather than increasing the length of the eyelets (longitudinally of the catheter). This is because increasing the width provides for the direct inflow into the catheter at a lower point than increasing the length.

In an embodiment of the invention, the first aspect is combined with the second aspect, so the invention provides an intermittent urinary catheter having a generally triangular cross-section with three substantially flat surfaces connected by rounded corners and two eyelets positioned equidistantly from the tip in two of the surfaces.

In a further embodiment, three eyelets may be positioned equidistantly from the tip, one eyelet in each of the three substantially flat surfaces.

The triangular cross-section provides for the possibility of positioning the eyelets so they are not opposite each other. In other words, the eyelets are positioned with an angle different from 180 degrees between each other around the circumference of the catheter cross-section. Positioning of two eyelets directly opposite each other may lead to weakening of the cross-section of the catheter at the eyelets. Thus, the catheter may have a tendency to collapse at this point during insertion.

By positioning the eyelets with an angle of approximately 120 degrees between around the circumference, this effect is avoided.

In an embodiment of the invention, the catheter is conical so that the inner cross-sectional area increases from the proximal insertion end to the distal end. In a related embodiment, the cross-sectional area increases corresponding to at least one CH size.

By increasing the cross-sectional area at least one CH size, the degree of laminar flow with respect to turbulent flow inside the catheter will increase. Laminar flow is the fastest possible flow through a tube, thus it is desirable to achieve a high degree of laminar flow through the catheter.

In a related embodiment, the cross-sectional area increases corresponding to at least two CH sizes. In an example, the insertion end has a cross-sectional area corresponding to a CH10 and the distal end has a cross-sectional area corresponding to a CH14.

A further advantage of a conical catheter is that users may have to use a rather thin catheter (CH8 or CH10) for various reasons (e.g. narrow passage around the prostate) and previously had to live with the increased drainage time that was the effect of that. With a conical catheter this drawback is eliminated because the user can use a catheter having a CH10 as the insertion end and a CH14 as the distal end and thus experience a flow corresponding to a regular CH14.

A third aspect of the invention relates to an intermittent urinary catheter having a volumetric flow of at least 15 ml/s when measured at a pressure of 400 mm $H_2O$.

The measurement of the volumetric flow is performed according to the standard DS/EN 1618:1997. Instead of measuring for at least 30 s as mentioned in the standard, the time to empty 200 ml were used. The catheter is attached to a constant level tank by attaching it in a central hole in a rubber stopper attached to a plastic tube that in turn is attached to a tapered connector on the constant level tank.

As mentioned in the Background supra, pressures of 400 mm $H_2O$ are normal for a user who is about to empty his or her bladder. With a volumetric flow of at least 15 ml/s, a catheter user will be able to empty the bladder as fast as a non-catheter user, because this flow is within the normal range of emptying for women.

DETAILED DESCRIPTION OF THE DRAWING

Initially, it shall be noted that the figures are schematic illustrations intended only to address the principles and functions of the base plate according to the invention and are not to be considered limiting to the scope of the attached claims. Furthermore, the figures and particularly the individually illustrated elements are not necessarily to scale, neither individually nor in relation to each other.

Figure 2:
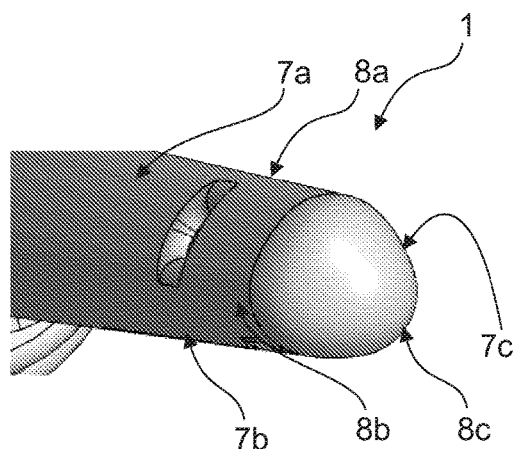
FIG. 2 illustrates a view seen from above of an embodiment of a catheter according to the invention.
Figure 3:
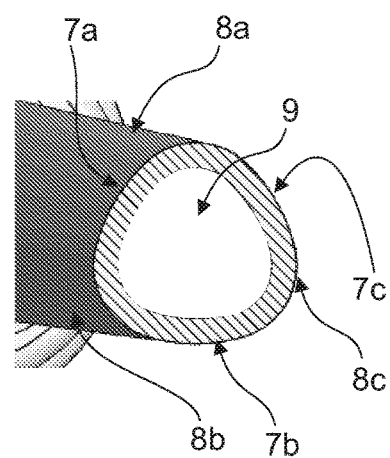
FIG. 3 illustrates a cross-sectional view of an embodiment of a catheter according to the invention.

FIGS. 1-3 illustrate an embodiment of a catheter 1 according to the invention. FIG. 1 illustrates a perspective view of the catheter 1, FIG. 2 illustrates a view of the catheter seen from above and FIG. 3 illustrates a cross-sectional view of the catheter.

The catheter 1 has a proximal insertion end 2 and a distal end 3. In the proximal end 2, the catheter is provided with a rounded tip 4 and in the distal end 3, the catheter is provided with a connector 5. Furthermore, there is at least one eyelet 6 near the proximal end 2 of the catheter. From FIGS. 2 and 3 it appears that the cross-section of the catheter is generally triangular with three substantially flat surfaces 7a, 7b, 7c connected by rounded corners 8a, 8b, 8c. The cross-section of the catheter is hatched and the inner cross-sectional area is indicated at 9 in FIG. 3.

Figure 4:
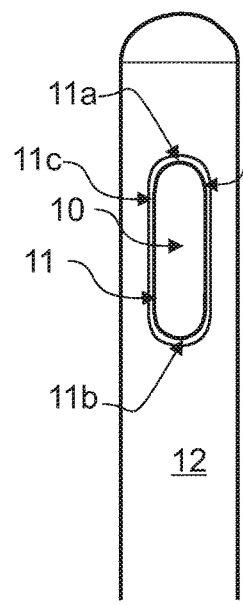
FIGS. 4 to 6 illustrate the difference between the position of the eyelets in a catheter with a generally circular cross section (FIG. 5) and in a catheter with a generally triangular cross-section (FIG. 6).
Figure 5:
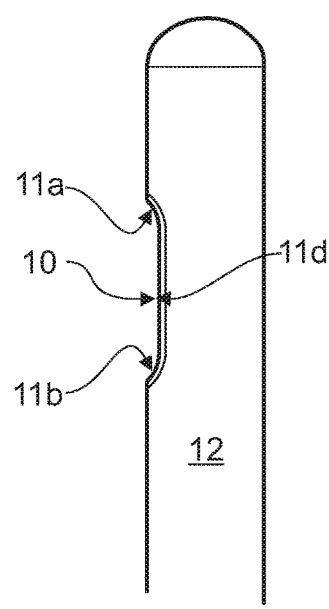
Figure 6:
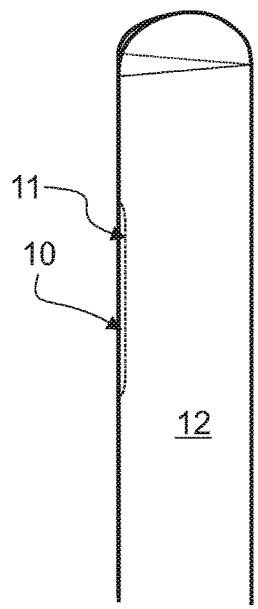

FIGS. 4 to 6 illustrate the difference between the position of the eyelets in a catheter with a generally circular cross section (FIG. 5) and in a catheter with a generally triangular cross-section (FIG. 6). FIG. 4 illustrates an eyelet 10 seen from the front or from the face. As can be seen in FIG. 4, the eyelet 10 is oval having a larger dimension in the longitudinal direction of the catheter and is provided with a rounded edge 11. The surface of the catheter is indicated at 12. The edge 11 has four major parts, top 11a and bottom 11b extending transversely of the catheter and two sides 11c, 11d, extending in the longitudinal direction of the catheter.

FIG. 5 illustrates a schematic drawing of the position of the eyelet 10 in a catheter with generally circular cross section and how the two sides 11c, 11d of the edge is positioned lower in the surface 12 than the top 11a and bottom, respectively. This positioning of the edge 11 of the eyelet may lead to chafing of the mocusal tissue inside the urethra.

FIG. 6 illustrates a schematic drawing of the position of the eyelet 10 in a catheter with generally triangular cross section. From this figure it can be seen that all four parts (11a, 11b, 11c and 11d) of the edge are positioned generally at the same level with respect to the surface 12. The dotted line indicates the rounding of the edge 11.

Figure 7A:
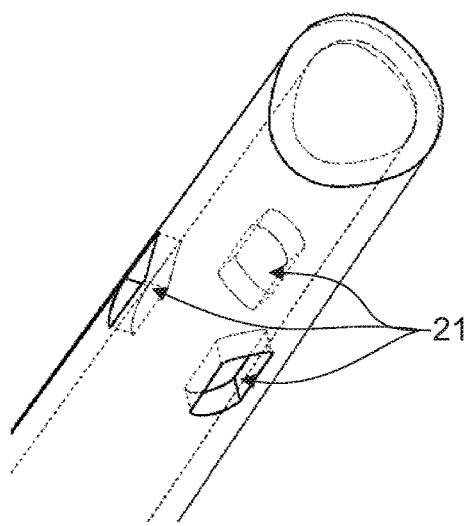
FIGS. 7A and 7B illustrate an embodiment of a catheter according to the invention, with three eyelets positioned at the same height.
Figure 7B:
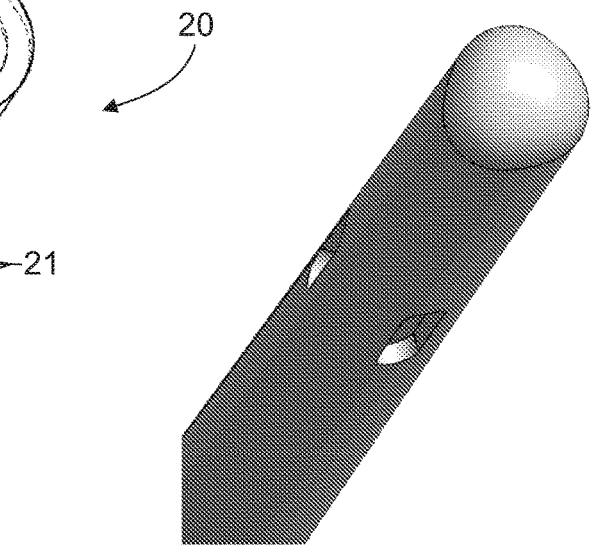

FIGS. 7A and 7B illustrate partly an embodiment of a catheter 20 according to the invention, with three eyelets 21 positioned at the same height. FIGS. 8 and 9 illustrate cross sections of catheters having three eyelets at the same height. In FIG. 8, a catheter 30 with a circular cross section is illustrated and in FIG. 9, a catheter 40 with a triangular cross section is illustrated. The cross-section is shown hatched and the eyelets are indicated at 31, 32 and 33 in FIG. 8 and at 41, 42 and 43 in FIG. 9. From the figures, it is clear that in the triangular catheter 40, the material left at the cross-section, indicated at 44, 45 and 46, will provide for triangular structures, whereas in the circular catheter, the material left at the cross section, indicated at 34, 35 and 36 will provide for arcuate structures. Triangular structures are the strongest possible structures because of the inability of the parts of the triangle to move with respect to each other. Therefore, the structure in FIG. 9 will be much stronger than the structure in FIG. 8 and thus a catheter having a cross-section as shown in FIG. 9 will be able to withstand buckling better than a catheter having a cross-section as shown in FIG. 8.

FIG. 10 illustrates the test set-up 100 used for the tests. The test set-up 100 includes a water tank 101 with an inlet tube 102 and an outlet tube 103. Furthermore, an overflow tube 104 is provided. The outlet tube is provided with a tap 104 for opening and closing the outlet—and a rubber stopper 105 for closing the tube. In use, a catheter provided with a modified rubber stopper is inserted in the outlet tube 103 in place of the rubber stopper 105. The inlet tube 102 is connected to a water supply so that water continuously flows into the water tank 101. The overflow tube 104 ensures that the level in the water tank is kept constant, thus ensuring that the pressure difference is constant and the correct volumetric flow through the catheter is measured. The tap 104 is opened and water drains through the catheter until the measurement is finished—see description in the Examples below.

EXAMPLES

Tests were done on intermittent female catheters. As mentioned in the Background supra, females that are not catheter users are able to empty their bladder with a volumetric flow rate of 24 ml/s in average. A known catheter CH12 has a volumetric flow rate of about 9 ml/s in average (8.9 ml/s). This means that in average a catheter user takes up to three times as long time as a non-catheter user to empty their bladder. Different geometries of female catheters were tested to show which geometries influence the flow rates and by how much.

The catheters were tested according to standard DS/EN 1618:1997. The testing was for all types of catheters done at a water column pressure of 400 mm H2O. The time it takes to empty 200 ml was measured.

The test set-up is shown in FIG. 10.

For all tests 5 measurements were done on each catheter, as described in the process for testing below:

1. Insert a rubber stopper with a centre hole corresponding largely to the circumference of the catheters to be tested in a 24 cm plastic tube.
2. Connect the plastic tube to the constant level tank and let the water flow through the tube for a couple of seconds, then close the valve.
3. Insert a test catheter through the stopper, and start the water flow. Control that the inlet still maintains a constant level while draining, if not increase the inflow. Repeat until the correct inflow is observed.
4. Align the plastic tube fitting at the constant level tank, so that the correct water column pressure is obtained: 400 mm from water surface to bottom of the lower edge of the lower eyelet of the catheter.
5. Turn on the water faucet and fill the water tank so the constant level is placed at the overflow channel and maintain the filling. Measure the distance from the water surface to the lower eye and adjust the plastic tube so that a distance of exactly 400 mm from water surface to lower edge of lower eyelet of the catheter is obtained.
6. Pull out the test catheter.
7. Insert a catheter to be tested.
8. Put a finger under the plunger and the open the valve. Eliminate air bubbles in the tube and valve by snapping at the plastic tube and faucet. Close the valve and remove the finger.
9. Start the stopwatch simultaneously with opening the valve.
10. When the water reaches 200 ml in the measuring cylinder close the valve and stop the stopwatch.
11. Place the filled measuring cylinder on a scale; subtract the weight of the empty measuring cylinder to obtain a more precise measure of how much water passed through. Take the amount of water in ml (1 ml=1 g) and divide it by the time you measured on the stop watch. Write down how many ml/s ran through.
12. Empty the measuring cylinder and shake it a couple of times to remove excess water, and pull out the catheter tip and shake a couple of times.
13. Repeat step #7-12 until there are 5 measurements for the catheter.

All tested catheters were 3D-printed using a printer called ProJet HD 3000 plus from 3DSystems and material called VisiJet EX200. Initial tests shown that the flow through the catheter may increase by 15% by using printed catheters as opposed to regular catheters (10.5 ml/s for a printed CH12 catheter compared to 8.9 ml/s for a regular CH12 female catheter). This is thought to be due to the surface structure.

The dimensions of the eyelets for test series 1 to 6 were a width (in the transverse direction of the catheter) of 0.9 mm and a height (in the longitudinal direction of the catheter) of 3.4 mm. The test series were as follows:

Series 1: 2×triangular catheter with one eyelet. The eyelet is positioned with the center 19 mm from the tip.

Series 2: 2×triangular catheter with two eyelets positioned with the center 19 mm from the tip.

Series 3: 2×triangular catheter with three eyelets, one on each side, all positioned with the center 19 mm from the tip Series 4: 2×triangular catheter with two eyelets, one eyelet positioned with the center 19 mm from the tip and one eyelet positioned with center 7 mm from the tip.

Series 5: 2×round catheter with two eyelets. One eyelet positioned with the center 19 mm from the tip and one eyelet positioned with the center 7 mm from the tip.

Series 6: 2×triangular catheter with three eyelets, placed exactly as the one described above. Conical with a cross-sectional area of a CH10 at the tip, and a CH14 at the outlet.

Series 7: 2×triangular catheter with three eyelets, placed exactly as the one described above. Conical with a cross-sectional area of a CH10 at the tip, and a CH14 at the outlet. The width of the eyelets is increased by 20% with respect to series 6 (width of eyelets 1.1 mm).

Series 8: 2×triangular catheter with three eyelets, placed exactly as the one described above. Conical with a cross-sectional area of a CH10 at the tip, and a CH14 at the outlet. The width of the eyelets is decreased by 20% with respect to series 6 (width of eyelets 0.72 mm).

Series 9: 2×triangular catheter cut-off below the eyelets to create direct inflow into the catheter tube. Conical with a cross-sectional area of a CH10 at the tip, and a CH14 at the outlet.

Results

The results of testing are shown in the table below. The mean-value for the series corresponds to the mean of testing 2 catheters, each tested 5 times as described above. Thus, the mean value is the mean of 10 tests.

TABLE 1

| Test series | Catheter type: | Mean ml/s | Standard deviation |
|---|---|---|---|
| 1 | Triangular, ONE eyelet 19 mm from tip | 8.6 | 0.33 |
| 2 | Triangular, TWO eyelets 19 mm from tip | 11.1 | 0.40 |
| 3 | Triangular, THREE eyelets 19 mm from tip | 12.5 | 0.51 |
| 4 | Triangular, TWO eyelets, 7 mm/19 mm from tip | 10.5 | 0.29 |
| 5 | Round, TWO eyelets, 7 mm/19 mm from tip | 10.6 | 0.33 |
| 6 | Triangular, Conical, three eyelets CH10-->CH14 | 17.3 | 0.70 |
| 7 | Triangular, Conical, three eyelets CH10 --> CH14, eyelets 20% larger | 18.9 | 0.26 |
| 8 | Triangular, Conical, three eyelets CH10 --> CH14, eyelets 20% smaller | 15.8 | 0.38 |
| 9 | Triangular, Conical, three eyelets CH10 --> CH14, suction | 19.3 | 0.58 |

Comparing test series 4 and 5 illustrates that by using a triangular catheter instead of a round catheter, the flow decreases slightly however the difference is so small it is not significant. Thus, it is possible to use a triangular catheter and obtain the benefits with respect to reduced microtraumas in the urethra due to the eyelets without influencing the flow through the catheter significantly.

Comparing test series 1 to 3 illustrates that there is a large benefit of increasing the number of eyelets in the same height (equidistantly from the tip) from one to three. The flow through the catheter increases by almost 50%. This can be explained by the theory above—that if the total area of eyelets at the same height (equidistantly from the tip) are at least as large as the cross-sectional area of the catheter, then the eyelets will not be the limiting factor with respect to flow.

Comparing test series 3 and 6 illustrates that by making the catheter conical an increase in the flow of more than 60% is obtained. As mentioned above, this is because the flow will be more laminar in a conical catheter and less turbulent. Laminar flow is to be aimed for since this is the fastest flow possible through a tube.

Comparing test series 6 to 8 illustrates the influence of the width of the eyelets. When the width of the eyelets is 20% higher, the flow is increased by almost 10%. Likewise a decrease in the width of the eyelets by 20% leads to a decrease in the flow by almost 10%.

Finally comparing test series 7 and 9 illustrates that by increasing the width of the eyelets by 20%, it is possible to obtain almost the same flow through the catheter as that obtainable by a suction catheter—that is a catheter having no tip and eyelets but just being cut-off at the position of the eyelets. The difference in flow between series 7 and 9 is not significant.

In conclusion, the test shows that the optimal catheter with respect to flow is a triangular catheter having three eyelets in the same height and having a cross-sectional area which increases from an area corresponding to a CH10 at the tip and to a CH14 at the outlet. Even if the results were reduced by 15% to compensate for the possible influence in material difference (printed material vs. regular catheter material), a catheter as in series 7 (reduced by 15%→flow=16.1 ml/s) would still provide a flow within the region of flows for non-catheter users. Thus, a catheter user should be able to empty their bladder as fast as a non-catheter user.

The invention claimed is:

1. An intermittent urinary catheter comprising:
    a catheter body extending from a distal end to a closed proximal end, where the catheter body between the distal end and the closed proximal end has a generally triangular shape in lateral cross-section formed by three surface segments connected by rounded corners, where an exterior surface of each of the three surface segments, between one of the rounded corners to a next adjacent rounded corner, has a convex curvature such that a surface length in the lateral cross-section is longer than a chord length of each of the three surface segments, where the chord length is measured from the one of the rounded corners to the next adjacent rounded corner; and
    an eyelet positioned in at least one of the three surface segments.

2. The intermittent urinary catheter according to claim 1, wherein each of the three surface segments has approximately equal area.

3. The intermittent urinary catheter according to claim 1 comprising at least two eyelets, each of the at least two eyelets is positioned equidistantly from the closed proximal end of the catheter body.

4. The intermittent urinary catheter according to claim 1 comprising three eyelets, each of the three eyelets is positioned equidistantly from the closed proximal end of the catheter body.

5. The intermittent urinary catheter according to claim 1, comprising three eyelets, with each of the three eyelets formed in one of the three surface segments.

6. The intermittent urinary catheter according to claim 1, wherein a first inner cross-sectional area of a lumen formed inside of the catheter body measured at a proximal location of the catheter body is smaller than a second inner cross-sectional area of the lumen formed inside of the catheter body measured at a distal location of the catheter body.

7. The intermittent urinary catheter according to claim 6, wherein a difference between the first inner cross-sectional area and the second inner cross-sectional area is at least one CH size.

8. The intermittent urinary catheter of claim 1, wherein the catheter body has a lumen formed inside of the catheter body, the lumen having a triangular cross-sectional shape that configures flow through the catheter body of at least 15 ml/s when measured at a pressure of 400 mm $H_2O$.

9. The intermittent urinary catheter of claim 1, wherein each of the rounded corners has a first radius of curvature and the convex curvature of the exterior surface of each of the three surface segments has a second radius of curvature, and the second radius of curvature is larger than the first radius of curvature.

10. The intermittent urinary catheter of claim 9, wherein the second radius of curvature is larger by a factor of about 10 than the first radius of curvature.

11. The intermittent urinary catheter of claim 1, wherein an entirety of the eyelet is positioned in a plane of the at least one of the three surface segments.

12. An intermittent urinary catheter comprising:
    a catheter body extending from an opening formed in a distal end to a proximal end, the proximal end is formed as a closed tip that is rounded and configured for insertion into an urethra;
    with the catheter body having a curved triangular shape in lateral cross-section formed by a first curved convex exterior surface connected to a second curved convex exterior surface by a first rounded corner, and a curved convex third exterior surface connected to the first curved convex exterior surface by a second rounded corner and connected to the second curved convex exterior surface by a third rounded corner, where the first curved convex exterior surface has a first arc length in the lateral cross-section that is longer than a first chord length of the first curved convex exterior surface, where the first chord length is measured from the first rounded corner to the second rounded corner; and at least one eyelet formed in at least one of the first curved convex exterior surface, the second curved convex exterior surface, and the third curved convex exterior surface.

13. The intermittent urinary catheter of claim 12, wherein the at least one eyelet comprises:
a first eyelet is formed in the first exterior surface,
a second eyelet is formed in the second exterior surface, and
a third eyelet is formed in the third exterior surface.

14. The intermittent urinary catheter of claim 12, wherein the second curved convex exterior surface has a second arc length in the lateral cross-section that is longer than a second chord length of the second curved convex exterior surface, where the second chord length is measured from the first rounded corner to the third rounded corner.

15. The intermittent urinary catheter of claim 12, wherein the third curved convex exterior surface has a third arc length in the lateral cross-section that is longer than a third chord length of the third curved convex exterior surface, where the third chord length is measured from the second rounded corner to the third rounded corner.

16. The intermittent urinary catheter of claim 12, wherein a radius of curvature of the first curved convex exterior surface and the second curved convex exterior surface is larger than a radius of curvature of the first rounded corner.

* * * * *